United States Patent
Walther

(10) Patent No.: US 6,612,700 B2
(45) Date of Patent: Sep. 2, 2003

(54) DEVICE FOR TESTING VISUAL FUNCTIONS OF THE HUMAN EYE

(75) Inventor: Hansueli Walther, Baden (CH)

(73) Assignee: Interzeag AG (CH)

( * ) Notice: Subject to any disclaimer, the term of this patent is extended or adjusted under 35 U.S.C. 154(b) by 76 days.

(21) Appl. No.: 09/939,864

(22) Filed: Aug. 27, 2001

(65) Prior Publication Data

US 2002/0047995 A1 Apr. 25, 2002

(30) Foreign Application Priority Data

Sep. 21, 2000 (EP) .............................. 00810866

(51) Int. Cl.[7] ................................. A61B 3/02
(52) U.S. Cl. ....................................... 351/224
(58) Field of Search ................. 351/208, 209, 351/221, 223, 224, 226, 245, 246

(56) References Cited

U.S. PATENT DOCUMENTS

| | | |
|---|---|---|
| 2,855,821 A | 10/1958 | Cuppers et al. ............ 88/20 |
| 5,125,731 A | 6/1992 | Fiorini et al. |
| 5,387,952 A | 2/1995 | Byer |
| 5,903,336 A | 5/1999 | Kohayakawa |
| 6,045,227 A | 4/2000 | Stewart et al. |
| 6,086,205 A | * 7/2000 | Svetliza ..................... 351/221 |

FOREIGN PATENT DOCUMENTS

| | | | |
|---|---|---|---|
| EP | 0 850 591 A1 | 7/1998 | ............ A61B/3/15 |
| GB | 326053 | 3/1930 | |
| WO | WO 00/13571 | 3/2000 | ............ A61B/3/00 |

* cited by examiner

*Primary Examiner*—George Manuel
(74) *Attorney, Agent, or Firm*—Webb Ziesenheim Logsdon Orkin & Hanson, P.C.

(57) ABSTRACT

A perimeter for visual examination has a head restraint and a control panel. Located on a unit base is an optical system, in which there is an optical examination system with an eyepiece. The optical system is movably mounted on the unit base and can be adjusted by means of at least one drive. The optical system can be tracked for precise positioning with respect to the eye being examined. The perimeter makes it possible to position the optical system in essentially any desired position.

6 Claims, 2 Drawing Sheets

DEVICE FOR TESTING VISUAL FUNCTIONS OF THE HUMAN EYE

CROSS-REFERENCE TO RELATED APPLICATION

This application claims priority to European Application No. 00 810 866.4 filed Sep. 21, 2000 and herein incorporated by reference in its entirety.

BACKGROUND OF THE INVENTION

1. Field of the Invention

This invention relates to a perimeter for testing the field of vision of a patient, the device having a head restraint for positioning the head of a patient, a control panel and a unit base on which an optical system with an eyepiece is located, in front of which the patient's head is to be positioned.

2. Description of the Prior Art

Automatic perimeters for the testing of the field of vision are described in the prior art and are used both in research and in practice for routine examinations. A perimeter of this type is commercially available under the trade name OCTOPUS, for example. With this perimeter, the sensitivity of the retina to differences in light levels is determined at different locations in the field of vision using a computer-controlled process. For these examinations, it is essential that the patient hold his head in a predetermined position that is symmetrical for the left eye and the right eye with reference to a viewing axis. During this examination, the patient sits in front of the perimeter and by means of a head restraint, which consists essentially of a chin rest and a head rest, the head and the eye being examined are positioned in front of the eyepiece. The person conducting the tests sits opposite the person being examined and operates the perimeter by means of a control panel which is attached to the perimeter.

U.S. Pat. No. 5,125,731 describes a perimeter of the type described above in which the head rest and chin rest for the positioning of the patient's head and eye can be adjusted during the examination. However, this process of precisely positioning the patient's head interferes with the patient's concentration and inevitably has a negative effect on the length of the examination and the quality of the examination results. Perimeters in general are also quite bulky, and it is frequently difficult to position them appropriately in an examination room because consideration has to be given to the fact that suitable seated positions are required for the patient and for the operator respectively.

An object of the invention is to create a perimeter for examining the field of vision that eliminates or reduces the disadvantages described above and that also delivers accurate examination results because the patient is in a comfortable position and the device is simple and easy to operate.

SUMMARY OF THE INVENTION

The invention teaches that this object can be accomplished in a perimeter of the type described above but in which the optical system is movably mounted on the unit base and can be adjusted in the vertical and horizontal direction by means of a drive.

On the perimeter of the invention, the optical system is movably mounted on the unit base and can be adjusted with respect to the control panel. It is thereby possible to freely select the position between the patient and the operator. The operator and the patient no longer necessarily have to sit opposite each other or at another defined angle; the positions of the operator and the patient can be selected without restrictions, which is advantageous above all in small spaces. An additional advantage of the perimeter of the invention is that for the precise positioning of the eye being examined in front of the eyepiece, the optical unit can be tracked in all directions. Because in this case it is no longer necessary to adjust the head restraint, the patient's concentration is not disrupted during a precise positioning of this type.

Additional advantageous characteristics of the invention are disclosed in the dependent claims, in the following portion of the description and in the accompanying drawings.

BRIEF DESCRIPTION OF THE DRAWINGS

The invention is explained in greater detail below with reference to one exemplary embodiment that is illustrated in the accompanying drawings, in which.

DETAILED DESCRIPTION OF THE INVENTION

Figure 1:
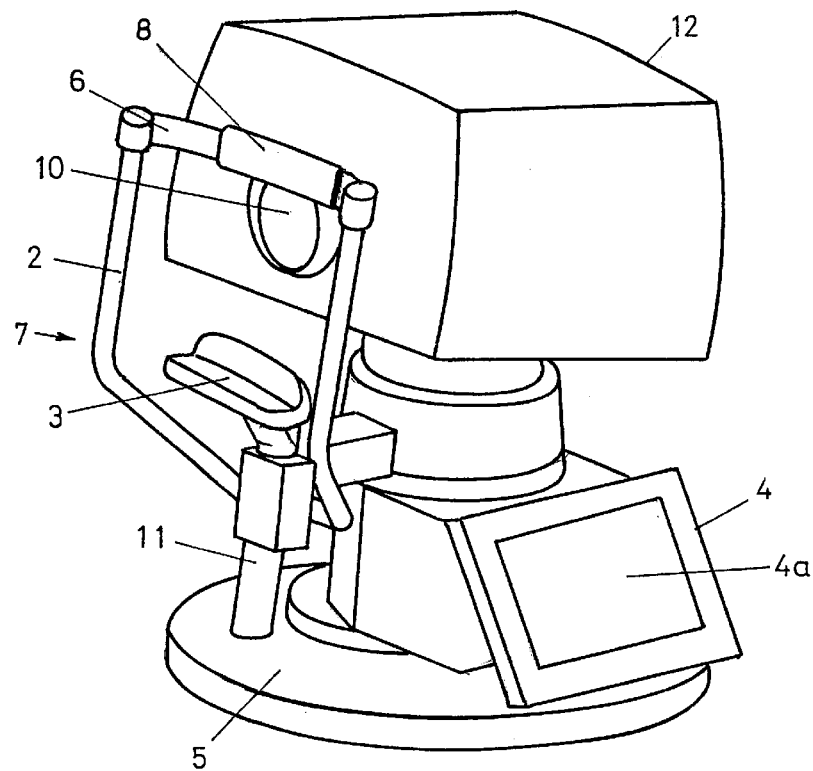
FIG. 1 is a schematic view in perspective of a perimeter of the invention.

The perimeter illustrated in FIG. 1 has a unit base 5 which can be positioned on a table, for example. A head restraint 7 is rotationally mounted on the unit base 5. A control panel 4 is also fastened to the unit base 5. From the control panel 4 the operator can operate the perimeter and supervise the examination. For this purpose the control panel 4 has a display 4a as well as keys and other control means not shown in the illustration.

The head restraint 7 has a chin rest 3 and two columns 2 to which the head rest 6 is fastened. Integrated into the head rest 6 are sensors 8 that automatically determine the position of the head. The height of the chin rest 3 can be adjusted by means of a spindle 11, and for its part, the head restraint 7 can be rotated around the unit base 5.

The patient positions his or her head in this head restraint 7 so that the left or right eye is correctly positioned with respect to the eyepiece 10 and the viewing axis.

Mounted in the unit base 5 is a column 9 which is vertically adjustable and on which an optical system 12 is installed which can be rotated around the column 9 and can be moved in the direction of the viewing axis. A conventional optical examination system of the prior art and the eyepiece 10, neither of which is shown in detail here, are integrated into the optical system 12.

Figure 2A:
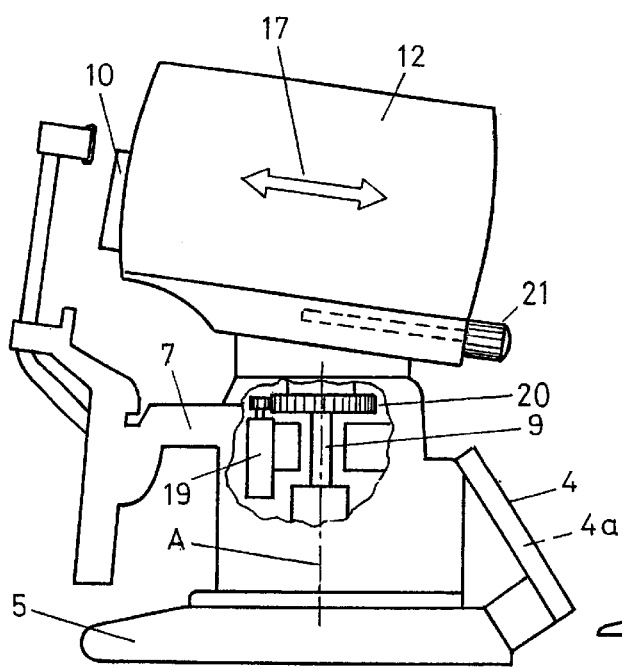
FIG. 2a is a rotated view of the perimeter of FIG. 1 with portions removed for ease of description.
Figure 2B:
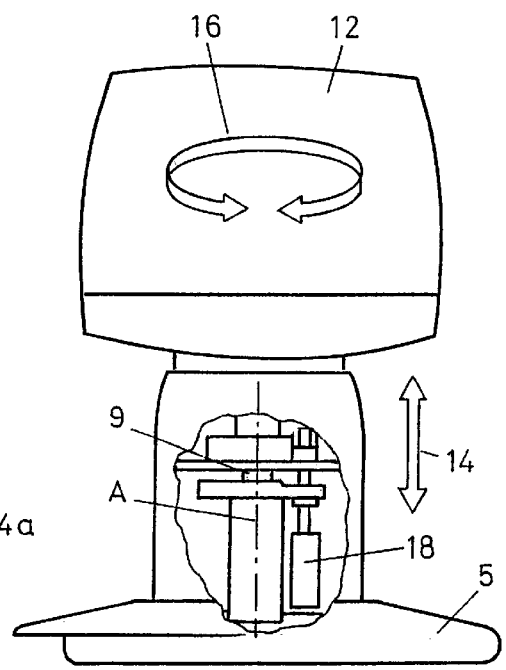
FIG. 2b is a rotated view of the perimeter of FIG. 2a with portions removed for ease of description.

FIG. 2b shows with the double arrow 14 the vertical adjustability of the column 9 and thus of the optical system 12. The double arrow 16 shows the rotation capability of the optical unit 12 on the vertical column 9 and the double arrow 17 (FIG. 2a) shows the displacement of the optical unit 12 in the direction of the viewing axis. A drive 18 is located in the unit base 5 for the vertical adjustment of the vertical column 9. The optical system 12 is rotated in the direction of the double arrow 16 by means of a drive 19 and a gear train 20. The optical system 12 is displaced in the direction of the viewing axis 17 by means of a mechanical spindle 21. All the drives can be electrical or other types of drives. The drives 18 and 19 can be controlled from the control panel 4. In the illustrated embodiment, the movement in the direction of the viewing axis 17 is controlled manually. The precise positioning can be controlled by using a camera to determine the position of the eye being examined and displaying the image on the display 4*a*.

The above description explains the movements that are desired for the precise positioning of the optical system with respect to the patient's eye that is being examined. To change the position between the patient and the operator, the optical system 12 is rotated into the desired position around the axis A. So that the patient can be positioned in front of the eyepiece, the head restraint 7 is rotated around the unit base 5 by the same angle. The control panel 4 remains firmly connected with the unit base 5 during all movements.

Figure 3A:
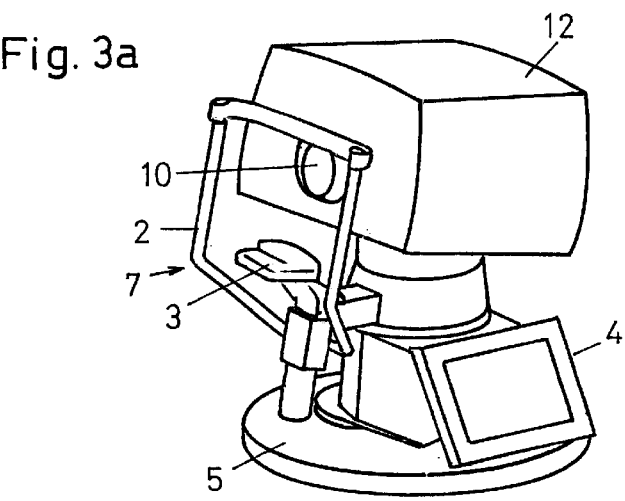
FIGS. 3a to 3c are each schematic illustrations of the perimeter of the invention with different orientations of the optical system.
Figure 3B:
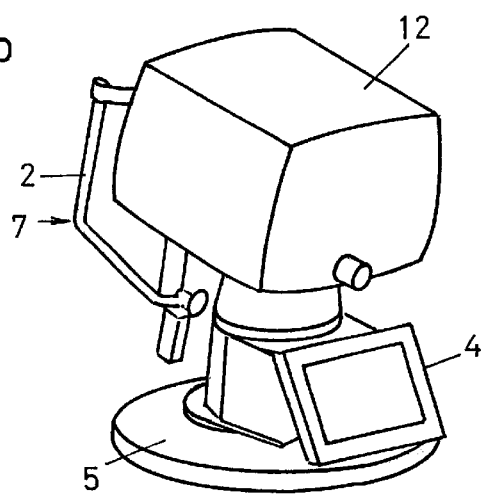
Figure 3C:
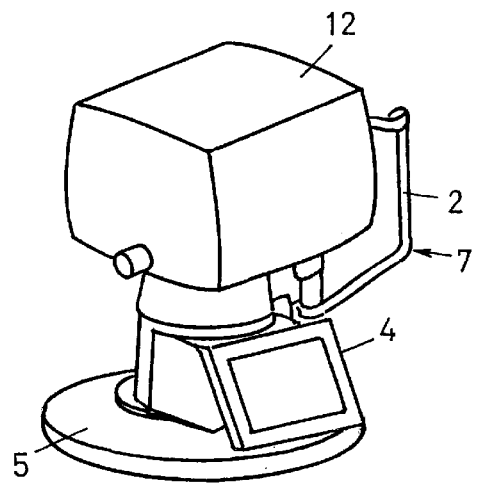

In the arrangement illustrated in FIG. 3*a*, the control panel 4, the optical system 12 with the eyepiece 10 and the head restraint 7 are arranged so that the patient sits on the operator's left. In the arrangement illustrated in FIG. 3*b*, the patient sits in the conventional position opposite the operator. Here, too, a precise positioning can be performed at any time by moving the optical system 12 in all three directions. In the arrangement illustrated in FIG. 3*c*, the patient sits on the operator's right. All intermediate positions are also possible in addition to the positions illustrated in FIGS. 3*a* to 3*c*.

Having described a presently preferred embodiment of the invention, it is to be otherwise appreciated that it is embodied within the scope of the appended claims.

I claim:

1. A perimeter for examining the field of vision comprising:

a head restraint having sensors to detect the position of a patient's head;

a control panel;

a unit base; and an optical system located on the unit base, which optical system includes an optical examination system with an eyepiece in front of which a patient's head is positioned, wherein the optical system is movably mounted on the unit base and is adjustable by at least one drive.

2. The perimeter as claimed in claim 1, wherein a position between a patient and an operator can be selected in essentially any desired positioning of the optical system and of the head restraint.

3. The perimeter as claimed in claim 2, wherein a position of the optical system can be tracked for precise positioning with respect to an eye being examined.

4. The perimeter as claimed in claim 3, wherein the precise positioning can be done manually or automatically.

5. The perimeter as claimed in claim 4, wherein the optical system is vertically adjustable by a vertical movement device.

6. The perimeter as claimed in claim wherein 3, wherein the optical system is movably mounted on a vertically adjustable column.

* * * * *

UNITED STATES PATENT AND TRADEMARK OFFICE
CERTIFICATE OF CORRECTION

PATENT NO. : 6,612,700 B2
DATED : September 2, 2003
INVENTOR(S) : Hansueli Walther It is certified that error appears in the above-identified patent and that said Letters Patent is hereby corrected as shown below:

Column 4,
Line 28, "claim wherein 3, wherein" should read -- claim 3, wherein --.

Signed and Sealed this

Third Day of February, 2004

JON W. DUDAS
*Acting Director of the United States Patent and Trademark Office*